United States Patent [19]

Bernstein et al.

[11] Patent Number: 5,049,576

[45] Date of Patent: Sep. 17, 1991

[54] CARBOXAMIDE DERIVATIVES

[75] Inventors: Peter R. Bernstein, Wallingford, Pa.; Frederick J. Brown, Newark; Victor G. Matassa, Wilmington, both of Del.; Ying K. Yee, Kennett Square, Pa.

[73] Assignee: ICI Americas Inc., Wilmington, Del.

[21] Appl. No.: 458,876

[22] Filed: Dec. 29, 1989

Related U.S. Application Data

[62] Division of Ser. No. 919,845, Oct. 16, 1986, Pat. No. 4,918,094.

[30] Foreign Application Priority Data

Oct. 17, 1985 [GB] United Kingdom ............... 8525658
Apr. 15, 1986 [GB] United Kingdom ............... 8609176

[51] Int. Cl.$^5$ ................... A61K 31/415; C07D 231/54
[52] U.S. Cl. .................................. 514/407; 514/406; 548/371; 548/372
[58] Field of Search ............... 548/371, 372; 514/406, 514/407

[56] References Cited

FOREIGN PATENT DOCUMENTS 0179619 4/1986 European Pat. Off. ............ 548/372
0007631 1/1970 France ................................ 548/371

OTHER PUBLICATIONS

Hannig et al., "Zur Kenntnis Einiger Derivate des 1-Benzyl-6-Aminoindazols", *Pharmazie* 29, H 10-11, 1974, pp. 685-686.

*Primary Examiner*—C. Warren Ivy
*Assistant Examiner*—Zinna Northington-Davis
*Attorney, Agent, or Firm*—Rosemary M. Miano; Thomas E. Jackson

[57] ABSTRACT

This invention provides a series of novel heterocyclic amides of formula I in which the group >X—Y—Z< is selected from >C=CH—N<, >C=N—N<, >N—(CH$_2$)—N<, >CH—CH$_2$—N< and >N—N=C< and the other radicals have the meanings defined in the following specification.

The compounds of formula I are leukotriene antagonists. The invention also provides pharmaceutically acceptable salts of the formula I compounds; pharmaceutical compositions containing the formula I compounds, or their salts, for use in the treatment of, for example, allergic or inflammatory diseases, or endotoxic or traumatic shock conditions; and processes for the manufacture of the formula I compounds, as well as intermediates for use in such manufacture.

12 Claims, No Drawings

5,049,576

CARBOXAMIDE DERIVATIVES

This is a divisional application of co-pending application Ser. No. 06/919,845 filed on Oct. 16, 1986 and now U.S. Pat No. 4,918,094.

SUMMARY AND BACKGROUND OF THE INVENTION

This invention concerns novel heterocyclic carboxamide derivatives and, more particularly, novel benzoic acids (and related tetrazoles and acylsulphonamides) derived from benzoheterocyclylcarboxamides, which antagonise the pharmacological actions of one or more of the arachidonic acid metabolites known as leukotrienes (hereinafter referred to as "leukotriene antagonist properties"). The novel derivatives are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions containing the novel derivatives for use in such treatments, and processes and intermediates for the manufacture of the novel derivatives.

In European patent application, publication number 0 166 591 A2 there are described indole-2-alkanoic acids and their use as prostaglandin antagonists and as inhibitors of the synthesis of leukotrienes. We have now discovered a series of benzoheterocyclic derivatives which have a carboxamidic substituent in the benzenoid ring and which unexpectedly possess the property of antagonising one or more of the arachidonic acid metabolites known as leukotrienes and this is the basis for our invention.

DESCRIPTION OF THE INVENTION

According to the invention there is provided a compound of formula I
(Formula set out on pages following Examples) I
wherein the group >X—Y—Z° is selected from a group consisting of:
  (a) >C=CH—N<
  (b) >C=N—N<
  (c) >N—(CH$_2$)$_2$—N<
  (d) >CH—CH$_2$—N<
  (e) >N—N=C< in which ">" and "<" indicate two separate bonds and wherein:

A is a direct link when Z is nitrogen and A is oxygen when Z is carbon;

$R^1$ is (2-10C)alkyl optionally containing 1 or more fluorine substituents; or $R^1$ is phenyl-(1-6C)alkyl in which the (1-6C)alkyl moiety may optionally bear a fluoro or (1-4C)alkoxy substituent and in which the phenyl moiety may optionally bear a substituent selected from the group consisting of halogeno, (1-4C)alkyl, (1-4C)alkoxy and trifluoromethyl; or $R^1$ is (3-8C)cycloalkyl or (3-8C)cycloalkyl-(1-6C)alkyl, the cyclic moiety of any of which optionally may contain one unsaturated linkage and may optionally bear 1 or 2 (1-4C)alkyl substituents;

Ra is hydrogen or methyl:

Rc is selected from a group consisting of hydrogen and (1-4C)alkoxy;

Rd is hydrogen, (3-8C)cycloalkyl, (3-8C)cycloalkyl-(1-4C)alkyl or (1-10C)alkyl optionally containing one or two double or triple bonds, said (1-10C)alkyl additionally optionally bearing a substituent P selected from a group consisting of cyano, carboxy, 1H-tetrazol-5-yl, (1-4C)alkoxycarbonyl, carbamoyl of formula CONR$^2$R$^3$, ureido of formula NR$^4$CONR$^2$R$^3$, carbamoyloxy of formula OCONR$^2$R$^3$, a carbamate of formula NR$^4$COOR$^5$, acylamino of formula NR$^4$COR$^5$, acyloxy of formula OCOR$^5$, and an (optionally oxidized) thio group of formula S(O)$_n$R$^5$ in which $R^2$ is chosen from a group consisting of hydrogen, (1-6C)alkyl, and phenyl, the phenyl moiety of which may optionally bear 1 or 2 substituents selected from a group consisting of halogeno, (1-4C)alkyl, (1-4C)alkoxy and trifluoromethyl: and $R^3$ and $R^4$ are independently chosen from a group consisting of hydrogen and (1-6C)alkyl: or $R^2$ and $R^3$ together with the adjacent nitrogen form a pyrrole, pyrrolidine, piperidine, morpholine, piperazine or N-(1-6C)alkylpiperazine ring:

$R^5$ is chosen from a group consisting of (1-4C)alkyl and phenyl, the phenyl moiety of which may optionally bear 1 or 2 substituents selected from a group consisting of halogen, (1-4C)alkyl, (1-4C)alkoxy and trifluoromethyl: and n is the integer 0, 1 or 2; and M is an acidic group selected from a group consisting of carboxy, an acylsulphonamide residue of formula —CO NH SO$_2$R$^6$ and 1H-tetrazol-5-yl in which $R^6$ is selected from a group consisting of (1-6C)alkyl, (3-8C)cycloalkyl, (6-12C)aryl, heteroaryl comprising 5-12 atoms at least one of which is carbon and at least one of which is selected from oxygen, sulfur, and nitrogen, and (6-12C)aryl-(1-4C)alkyl, in which any of the aromatic or heteroaromatic moieties may bear 1 or 2 substituents selected from a group consisting of halogeno, amino, (1-4C)alkyl, (1-4C)alkoxy, and trifluoromethyl;

or a pharmaceutically acceptable salt thereof.

It will be appreciated that certain of the compounds of formula I, for example those wherein $R^1$ contains an asymmetrically substituted carbon atom, may exist in, and be isolated in, optically-active and racemic forms. In addition, it will be appreciated that certain compounds of formula I, for example, those wherein Rd contains a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and from optically-active starting materials) and individual 'E' and 'Z' stereoisomers (for example, by chromatographic separation of a mixture thereof) and how to determine the leukotriene antagonist properties by the standard tests described hereinafter.

In this specification P, M, $R^1$, Rc et cetera stand for generic radicals and have no other significance. It is to be understood that the generic term "(1-6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno is fluoro, chloro, bromo or iodo.

Included in the ranges and values for the generic radicals are those wherein:

$R^1$ is selected from a group consisting of (3-7C)alkyl optionally containing 1 or more fluorine substituents; phenyl-(1-4C)alkyl in which the (1-4C)alkyl moiety may optionally bear a fluoro or (1-4C)alkoxy substituent and in which the phenyl moiety may optionally bear a substituent selected from the group consisting of halogeno, (1-4C)alkyl, (1-4C)alkoxy and trifluoromethyl; (3-6C)cycloalkyl and (3-6C)cycloalkyl-(1-4C)alkyl, the cyclic moiety of any of which optionally may contain one unsaturated linkage and may optionally bear 1 or 2 (1-4C)alkyl substituents;

Ra is hydrogen;

Rd is hydrogen, (3-6C)cycloalkyl, (3-6C)-cycloalkyl-(1-2C)alkyl or (1-5C)alkyl optionally containing one double or triple bond, said (1-5C)alkyl additionally optionally bearing a substituent P selected from a group consisting of cyano, carboxy, 1H-tetrazol-5-yl, (1-2C)alkoxycarbonyl, carbamoyl of formula $CONR^2R^3$, and an oxidized thio group of formula $S(O)_nR^5$ in which:

$R^2$ is chosen from a group consisting of hydrogen, (1-4C)alkyl, and phenyl, the phenyl moiety of which may optionally bear 1 or 2 substituents selected from a group consisting of halogeno, (1-4C)alkyl, (1-4C)alkoxy and trifluoromethyl; and $R^3$ is chosen from the group consisting of hydrogen and (1-4C)alkyl: or (2) $R^2$ and $R^3$ together with the adjacent nitrogen form a piperidine, morpholine, piperazine or N-(1-2C)alkylpiperazine ring;

$R^5$ is chosen from a group consisting of (1-4C)alkyl and phenyl wherein the phenyl moiety may optionally bear 1 or 2 substituents selected from a group consisting of halogen, (1-4C)alkyl, (1-4C)alkoxy and trifluoromethyl: and n is the integer 1 or 2:

or in which:

$R^2$ and $R^3$ are independently chosen from a group consisting of hydrogen and (1-4C)alkyl:

$R^5$ is (1-4C)alkyl: and n is the integer 1 or 2: and

M is an acidic group selected from a group consisting of carboxy, an acylsulphonamide residue of formula $—CO.NH.SO_2R^6$ and 1H-tetrazol-5-yl in which $R^6$ is selected from a group consisting of (1-4C)alkyl, (3-6C)cycloalkyl, phenyl, and heteroaryl comprising 5-6 atoms at least one of which is carbon and at least one of which is selected from oxygen, sulfur, and nitrogen, in which any of the aromatic or heteroaromatic moieties may bear 1 or 2 substituents selected from a group consisting of halogeno, amino, (1-4C)alkyl, (1 4C)alkoxy, and trifluoromethyl; or in which:

$R^6$ is selected from a group consisting of (1-4C)alkyl, phenyl, and heteroaryl comprising 5-6 atoms at least one of which is carbon and at least one of which is selected from oxygen, sulfur, and nitrogen, in which any of the aromatic or heteroaromatic moieties may bear 1 or 2 substituents selected from a group consisting of halogeno, amino, (1-4C)alkyl, (1-4C)alkoxy, and trifluoromethyl.

Particular values for the ranges of generic radicals described above under P, M, $R^1$, Rc et cetera are as follows:

for $R^1$ when it is (2-10C)alkyl is, for example, ethyl, propyl, isopropyl, butyl, isobutyl, sec-butyl, t-butyl, pentyl, 3-methylbutyl, 1-ethylpropyl, hexyl, heptyl, 1-ethylpentyl or nonyl; and when it contains 1 or more fluorine substituents a particular value is, for example, 2,2,2-trifluoroethyl.

Particular values for $R^1$ when it is phenyl(1-6C)alkyl include, for example, benzyl, 1-phenylethyl, 2-phenylethyl, 1-phenylpropyl, 2-phenylpropyl, -phenylpropyl, 1-methyl-1-phenylethyl, 1-phenylpropyl, 1-phenylbutyl and 1-phenylpentyl; and a particular value for an optional (1-4C)alkoxy substituent on the (1-6C)alkyl moiety is, for example, methoxy or ethoxy.

Particular values for certain optional substituents which may be present on a phenyl moiety of $R^1$, or as a part thereof, as defined above, include, for example:

for halogeno: a member selected from the group consisting of fluoro, chloro and bromo;

for (1-4C)alkyl: a member selected from the group consisting of methyl and ethyl; and for (1-4C)alkoxy: a member selected from the group consisting of methoxy and ethoxy.

A particular value for $R^1$ when it is (3-8C)cycloalkyl is, for example, cyclopropyl, cyclobutyl, cyclopentyl, cyclohexyl or cycloheptyl; when $R^1$ is (3-8C)cycloalkyl-(1-6C)alkyl a particular value is, for example, cyclobutylmethyl, cyclopentylmethyl, cyclohexylmethyl, 1-cyclopentylethyl, 2-cyclopentylethyl, 1-cyclopentylpropyl, 1-cyclohexylpropyl, 1-cyclopentylbutyl, 1-cyclohexylbutyl: and a particular value for $R^1$ when it is a radical containing an unsaturated linkage in the cycloalkyl ring is, for example, cyclopentenyl, cyclohexenyl, cyclopentenyl-(1-6C)alkyl (such as cyclopentenylmethyl) or cyclohexenyl(1-6C)alkyl (such as 1-cyclohexen-4-ylmethyl or 1-(cyclohexenyl)butyl): and a particular value for an optional (1-4C)alkyl substituent on the cyclic moiety of such a radical is, for example, methyl, ethyl or isopropyl.

A particular value for Rc when it is (1-4C)alkoxy is, for example, methoxy or ethoxy.

A particular value for Rd when it is (3-8C)cycloalkyl is, for example, cyclopropyl, cyclopentyl or cyclohexyl: when Rd is (3-8C)cycloalkyl-(1-4C)alkyl, a particular value is, for example, cyclopropylmethyl, cyclopentylmethyl or cyclohexylmethyl; when Rd is (1-10C)alkyl, a particular value is, for example, methyl, ethyl, propyl, isopropyl, butyl, isobutyl, sec-butyl, 3-methylbutyl, pentyl or hexyl: when Rd is an alkyl containing 1 or 2 double or triple bonds a particular value is, for example, vinyl, allyl, 1-propenyl, 2-methylallyl, 3-methylbut-2-enyl, 1,3-butadienyl, 1,3-pentadienyl, 2-propynyl or 3-butynyl, said alkyl group additionally optionally bearing a substituent P as defined above.

A particular value for P when it is (1-4C)alkoxycarbonyl is, for example, methoxycarbonyl, ethoxycarbonyl, or isopropoxycarbonyl:

A particular value for each of $R^2$, $R^3$, $R^4$, and the N-substituent of a piperazine when the particular group is (1-6C)alkyl is, for example, methyl, ethyl, propyl, isopropyl, butyl, t-butyl or pentyl.

A particular value for $R^5$ when it is (1-4C)alkyl is, for example, methyl, ethyl, propyl or isopropyl.

Particular values for optional substituents which may be present on a phenyl moiety of $R^2$ or $R^5$ include those defined above in connection with a phenyl moiety in $R^1$.

A particular value for $R^6$ when it is (1-6C)alkyl is, for example, methyl, ethyl, propyl, isopropyl or butyl: when $R^6$ is (3-8C)cycloalkyl a particular value is, for example, cyclopentyl or cyclohexyl: when $R^6$ is (6-12C)aryl a particular value is, for example, phenyl, 1-naphthyl or 2-naphthyl: when $R^6$ is heteroaryl a particular value is, for example, furyl, thienyl or pyridyl; and when $R^6$ is (6-12C)aryl-(1-4C)alkyl a particular value is, for example, benzyl, 1-naphthylmethyl or 2-naphthylmethyl.

Particular values for optional substituents which may be present on an aromatic or heteroaromatic moiety of $R^6$ include those defined above in connection with a phenyl moiety in $R^1$.

Thus, particular values for the radicals include for $R^1$: 3-methylbutyl and cyclopentylmethyl: for Ra: hydrogen and methyl: for Rc: methoxy: for Rd: methyl, 2-carbamoylethyl and 1-(N,N-dimethylcarbamoyl)ethyl: and for M: carboxy and an acylsulfonamide residue of formula —CO.NH.SO$_2$R$^6$ in which $R^6$ is 2-methylphenyl.

More particular values for the groups listed above include by way of example those selected from the groups consisting of: for $R^1$ ethyl, propyl, isopropyl, butyl, isobutyl, sec-butyl, t-butyl, pentyl, 3-methylbutyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, cyclopentyl, cyclohexyl, cyclobutylmethyl, cyclopentylmethyl, cyclohexylmethyl, 2-cyclopentylethyl, 1-cyclopentylbutyl, 1-cyclohexylpropyl, 1-cyclohexylbutyl, cyclopentenylmethyl, and 1-cyclohexen-4-ylmethyl;

for Rc: hydrogen and methoxy:

for Rd: methyl, ethyl, propyl, butyl, vinyl, allyl, 1-propenyl, 1,3-butadienyl and 2-propynyl, said group additionally optionally bearing a substiuent P as defined above:

for $R^2$ hydrogen, methyl, ethyl, propyl, isopropyl, t-butyl, phenyl, 2-methylphenyl and 4-chlorophenyl: for $R^3$ and $R^4$ (independently selected): hydrogen, methyl and ethyl;

for $R^2$ and $R^3$ together with the adjacent nitrogen: piperidine, morpholine, and N-methylpiperazine:

for $R^5$: methyl, ethyl, propyl, isopropyl, phenyl, 2-methylphenyl and 4-chlorophenyl: and for $R^6$ methyl, isopropyl, butyl, cyclopentyl, phenyl, 4-chlorophenyl, 4-methylphenyl, 2-chlorophenyl, 2-aminophenyl, 2-methylphenyl, 2-methoxyphenyl, 2-naphthyl, thien-2-yl and 6-chloropyrid-3-yl.

Examples of specific groups which are of special interest include those selected from the groups consisting of:

for $R^1$ cyclopentylmethyl;
for Rc: methoxy: and
for $R^6$ phenyl, 2-aminophenyl, 2-methylphenyl, 2-methoxyphenyl and 2-chlorophenyl.

It will be appreciated that within the above definitions there are included a number of sub-groups of compounds, for example:

(i) indoles of formula Ia;

(Formula set out on pages following Examples)　　Ia (ii) indazoles of formula Ib;

(Formula set out on pages following Examples)　　Ib (iii) tetrahydroquinoxalines of formula Ic:

(Formula set out on pages following Examples)　　Ic (iv) indolines of formula Id;

(Formula set out on pages following Examples)　　Id and (v) indazoles of formula Ie (Formula set out on pages following Examples)　　Ie together with the pharmaceutically acceptable salts thereof.

In the above sub-groups a preferred value for M is carboxy, 1H-tetrazol-5-yl or a radical of formula —CONH SO$_2$R$^6$ wherein $R^6$ is phenyl, optionally substituted as defined above, for example, 2-methylphenyl. A preferred value for $R^1$ is, for example, cyclopentylmethyl.

Preferred groups of compounds of the invention comprise the indole derivatives of formula IIa: (Formula set out on pages following Examples) IIa and the indazole derivatives of formula IIb: (Formula set out on pages following Examples) IIb wherein $R^1$, Ra, Rd and M have any of the meanings defined above: together with the pharmaceutically acceptable salts thereof.

Specific compounds of the invention are described in the accompanying examples. However, of those the compounds N-[4-[1-(2-carbamoylethyl)-5-(N-cyclopentylmethylcarbamoyl)indol-3-ylmethyl]-3-methoxybenzoyl]-2-methylbenzenesulphonamide and N-[4-[5-(N-cyclopentylmethylcarbamoyl)-1-[1-(N,N-dimethylcarbamoyl)ethyl]indol-3-ylmethyl]-3-methoxybenzoyl]2-methylbenzenesulphonamide are particularly preferred and may be used either in the free acid form or as corresponding pharmaceutically acceptable salts.

Examples of suitable pharmaceutically acceptable salts are salts formed with bases which form a physiologically acceptable cation, such as alkali metal (especially sodium and potassium), alkaline earth metal (especially calcium and magnesium), aluminum and ammonium salts, as well as salts made with appropriate organic bases such as triethylamine, morpholine, piperidine and triethanolamine. For those compounds of formula I which are sufficiently basic, examples of suitable pharmaceutically acceptable salts include acid-addition salts such as those made with a strong acid, for example hydrochloric, sulphuric or phosphoric acid.

The compounds of formula I may be made by processes which include processes well known in the chemical art for the production of structurally analogous heterocyclic compounds. Such processes for the manufacture of a compound of formula I as defined above are provided as further features of the invention and are illustrated by the following procedures in which the meanings of generic radicals are as defined above: L is defined as a (1-10C)alkylene group optionally containing one or two double or triple bonds: T is defined as a group selected from the group consisting of COORh (wherein Rh has the values defined below), CN, and the values defined above for M; U is defined as a suitable leaving group, for example, halogeno (especially chloro, bromo, or iodo) or alkane- or arene-sulphonyloxy (especially methanesulphonyloxy or p-toluenesulphonyloxy); and Hal is defined as halogeno, especially chloro, bromo or iodo.

(A) For those compounds wherein M is a carboxylic acid group, decomposing a suitable ester of formula III:

(Formula set out on pages following Examples)   III wherein Rh is a conveniently removed acid protecting group, for example, (1-6C)alkyl optionally bearing an acetoxy, (1-4C)alkoxy or (1-4C)alkylthio substituent, or phenyl or benzyl. A particular value for Rh is, for example, methyl, ethyl propyl, t-butyl, acetoxymethyl, methoxymethyl, 2-methoxyethyl, methylthiomethyl, or phenyl or benzyl.

Certain of the starting esters of formula III may be active in their own right as leukotriene antagonists (such as, for example, by in vivo conversion to the corresponding carboxylic acid), for example, those compounds wherein Rh is (1-6C)alkyl, and they are included within the scope of the invention.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when Rh is methyl, the ester may be decomposed by nucleophilic demethylation with, for example, lithium thioethoxide in a solvent such as N,N'-dimethylpropyleneurea. Alternatively, it may be possible in certain circumstances, for example, when Rh is t-butyl, to carry out the decomposition by thermal means, for example, by heating the ester of formula III at a temperature of, for example, 100°-150° C. alone or in a suitable solvent or diluent such as diphenylether. In addition, when Rh is t-butyl the decomposition may be performed, for example, by using trimethylsilyl triflate and then water, in a conventional manner. Still further, in certain circumstances, for example, when Rh is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°-200° C. and conveniently at or near ambient temperature. When such a method is employed, the resulting carboxylic acid of formula I, wherein M is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulphuric acid.

(B) Acylating an amine of formula $R^1$NHRa with a arboxylic acid (or a reactive derivative thereof) of formula IV:

(Formula set out on pages following Examples)   IV but wherein T is chosen from the values defined for M. When M is a carboxy group or P is a carboxy group, a preferred reactive derivative of the carboxy group shown in formula IV is a lower alkyl ester of that carboxy group, for example, the methyl ester.

When an acid halide derivative of an acid of formula IV is used as the acylating agent, a suitable base such as triethylamine, N-methylmorpholine, pyridine, 2,6-lutidine or 4-(dimethylamino)pyridine is conveniently also employed, preferably together with a suitable inert solvent or diluent, for example, dichloromethane, diethyl ether, tetrahydrofuran or 1,2-diemthoxyethane.

Alternatively, a suitable condensing agent, for example, a carbodiimide (such as dicyclohexylcarbodiimide or 1-(3-dimethylaminopropyl)-3-ethylcarbodiimide, or a salt thereof) or 1,1'-carbonyldiimidazole, may be employed with an acid of formula IV, preferably together with a suitable inert solvent or diluent, for example, N,N-dimethylformamide or one of those mentioned above for use with an acid halide.

When a lower alkyl ester of an acid of formula IV is used as the acylating agent, the reaction is preferably performed in the absence of any condensing agent of diluent in the presence of an excess of the amine $R^1$NHRa.

In general, the acylations are carried out at a temperature in the range of, for example, $-20°$ to 60° C. and, conveniently, at or near ambient temperature.

(C) Reacting a compound of formula V:

(Formula set out on pages following Examples)   V but wherein T is chosen from the values defined for M (which compound of formula V is thus a compound of formula I wherein Rd is hydrogen), with a reagent of formula U.Rd, an appropriate polarized vinyl reagent of formula $CH_2=CHP$ (optionally bearing additional alkyl substituents on the vinyl group), or an appropriate polarized ethynyl reagent of formula $CH=CP$. Appropriate polarized vinyl reagents include, for example, acrylamide, methyl acrylate, acrylonitrile, methyl vinyl sulfoxide, and phenyl vinyl sulfone. An appropriate polarized ethynyl reagent is, for example, methyl propiolate.

The reaction is preferably performed in the presence of a suitable base, for example, an alkali metal hydride such as sodium or potassium hydride in a suitable inert solvent or diluent, for example, tetrahydrofuran, 1,2-dimethoxyethane, N-methylpyrrolidone, or N,N-dimethylformamide. Alternatively, the compound of formula V may be used in the form of its preformed anhydrous alkali metal salt, for example, by prior reaction with a suitable base such as sodium or potassium methoxide, t-butoxide, or hydride, or butyl lithium; in which case a wider range of conventional solvents or diluents may be employed for the reaction with the alkylating agent. In either case, the alkylation is generally performed at a temperature in the range of, for example, $-10°$ C. to 40° C. and, conveniently, at or near ambient temperature.

(D) For a compound of formula I wherein $>X—Y—Z<$ has the value (a) defined hereinabove, reacting an indole of formula VI:

(Formula set out on pages following Examples)   VI with an alkylating agent of formula VII:

(Formula set out on pages following Examples)   VII but wherein T is chosen from the values defined for M, optionally in the presence of a suitable Lewis acid. A particularly suitable Lewis acid is, for example, silver oxide, silver carbonate, silver fluoroborate, silver trifluoroacetate, silver trifluoromethanesulfonate, zinc chloride, ferric chloride or stannic chloride.

The process is generally best performed in a suitable solvent or diluent, for example, in acetone; dichloromethane; acetonitrile; an ether solvent such as 1,2-dimethoxyethane, 1,4-dioxane or tetrahydrofuran; or a hydrocarbon solvent such as toluene or xylene; and at a temperature in the range of, for example 15°–140° C. and, more preferably, in the range of 80°–110° C.

Alternatively, in the absence of a Lewis acid catalyst, the process is generally best performed in a suitable solvent or diluent, for example, in a polar solvent (such as N,N-dimethylformamide, N,N'-dimethylpropyleneurea or N-methylpyrrolidone), or in an ether solvent (such as dioxane or 1,2-dimethoxyethane), optionally together with a hydrocarbon diluent such as toluene or xylene; and the alkylation is generally best performed at a temperature in the range of, for example, 50°–160° C., and, preferably, in the range of 80°–120° C.

(E) For a compound of formula I wherein M is a 1H-tetrazol-5-yl radical, reacting a cyano derivative of formula VIII:

(Formula set out on pages following examples)   . VIII with an azide. A particularly suitable azide is, for example, an alkali metal azide such as sodium or potassium azide, preferably together with an ammonium halide, for example, ammonium chloride or ammonium bromide or, especially, with triethylammonium chloride.

The reaction is preferably performed in a suitable polar solvent, for example, N,N-dimethylformamide or N-methylpyrrolidone, and conveniently at a temperature in the range of, for example, 50° to 160° C.

(F) For a compound of formula I wherein M is a group of formula CO NH SO$_2$ R$^6$, reacting a compound of formula I wherein M is carboxy (which compound is hereinafter referred to as "acid of formula I") with a sulphonamide derivative of formula R$^6$. SO$_2$. NH$_2$ in the presence of a dehydrating agent or by reacting a reactive derivative of the acid of formula I with a sulphonamide, or a salt thereof, of formula R$^6$ SO$_2$ NH$_2$.

Thus, for example, a free acid of formula I may be reacted with a suitable dehydrating agent, for example, with dicyclohexylcarbodiimide or 1-(3-dimethylaminopropyl)-3-ethylcarbodiimide, or with a hydrochoride or hydrobromide salt thereof, optionally together with an organic base, for example, 4-(dimethylamino)pyridine, and with a sulphonamide of formula R$^6$ SO$_2$ NH$_2$ in the presence of a suitable solvent or diluent, for example, dichloromethane, at a temperature in the range of, for example, 10° to 50° C., but preferably at or near ambient temperature.

Alternatively, a reactive derivative of an acid of formula I, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulphonamide of formula R$^6$. SO$_2$. NH$_2$, conveniently at or near ambient temperature and in a suitable solvent or diluent, for example, tetrahydrofuran, N,N-dimethylformamide or dichloromethane.

(G) For a compound of formula I wherein $>$X—Y—Z$<$ has the value (b) defined hereinabove, dehydration of an amino-oxime of formula IX:

(Formula set out on pages following Examples)   IX but wherein T is chosen from the values defined for M, by first reacting a compound of formula IX with a suitable condensing agent, for example, a carboxylic acid anhydride (such as acetic or propionic anhydride), preferably in a suitable solvent or diluent, for example a chlorinated hydrocarbon solvent (such as dichloromethane or dichloroethane) in the presence of an organic base (for example, 4-(dimethylamino)pyridine), followed by heating the resulting O-acyloxime, preferably under reduced pressure in the absence of solvent or diluent, but which heating may also be carried out in a suitable inert solvent or diluent, for example, a hydrocarbon solvent (such as toluene or xylene), and at a temperature in the range of 80°–250° C., but preferably in the range of 140°–200° C.

The dehydration of compounds of formula IX may also be carried out without prior derivatization to the acyl derivatives by heating, preferably in the absence of solvent or diluent, but which heating may also be carried out in a suitable solvent or diluent, such as these mentioned above, at a temperature in the range of 150°–300° C., but preferably in the range of 150°–250° C. Compounds of formula IX, but wherein T is chosen from the values defined for M, may be obtained, by standard procedures known in the art, from compounds of formula X:

(Formula set out on pages following Examples)   X but wherein T is chosen from the values defined for M, such compounds of formula X having been obtained from corresponding compounds of formula Ia by oxidative cleavage of the unsaturated linkage, using techniques known in the art.

(H) For a compound of formula I wherein $>$X—Y—Z$<$ has the value (b) defined above, a modified version of process (A) or (E) described above comprising cross coupling an indazole of formula XI:

(Formula set out on pages following Examples)   XI with a compound of formula VII, but wherein T is COORh or CN and wherein U is a halogeno which may be the same as the Hal of the indazole of formula XI or different, to afford a corresponding compound of formula III or VIII, wherein $>$X—Y—Z$<$ has the value (b) defined above; followed by conversion of the COORh group or the CN group, respectively, into one of the values defined above for M by application of process (A) or (E), respectively.

The cross coupling process may be carried out, for example, using a stoichiometric amount of activated zinc dust and a catalytic quantity of a transition metal catalyst, such as, for example, dichloro[1,1'-bis(diphenylphosphino)ferrocene]palladium(II) or dichlorobis(triphenylphosphine)nickel(II) to couple, for example, 3-bromo-5-(N-cyclopentylmethylcarbamoyl)-1-(carbamoylmethyl)indazole with, for example, methyl 4-bromomethyl-3-methoxybenzoate to afford methyl 4-[5-(N-cyclopentylmethylcarbamoyl)-1-(carbamoylmethyl)indazol-3-ylmethyl]-3-methoxybenzoate: followed by decomposition of the ester to afford 4-[5-(N-cyclopentylmethylcarbamoyl)-1-(carbamoylmethyl)indazol- 3-ylmethyl]-3-methoxybenzoic acid.

(I) For a compound of formula I wherein >X—Y—Z< has the value (c) or (e) defined above, alkylation of an imino compound of formula XII:

(Formula set out on pages following Examples) XII with an alkylating agent of formula VII, but wherein T is chosen from the values defined for M, in the presence of a suitable base, such as potassium carbonate or sodium methoxide, in a solvent such as acetone, methanol or N,N-dimethylformamide.

(J) For a compound of formula I wherein >X—Y—Z< has the value (d) defined above, catalytic hydrogenation of an indole of formula I wherein >X—Y—Z< has the value (a) defined above.

Particularly suitable catalytic hydrogenation conditions are those of catalytic transfer hydrogenation, for example, palladium on carbon (10% w/w) and formic acid (99%) at a temperature in the range of, for example, 15°–100° C., more preferably in the range of 70°–85° C.

(K) Reduction of the double bond of a compound of formula I in which Rd contains one double bond to provide a corresponding compound of formula I in which Rd contains no double bond.

Preferred reduction conditions include, for example, catalytic hydrogenation over palladium on carbon in a suitable solvent such as methanol, ethanol or tetrahydrofuran at ambient temperature, and, optionally, the addition of an equivalent of a base, such as, for example, potassium hydroxide or triethylamine.

(L) For a compound of formula I in which P is a carboxy group, decomposing an ester of formula XIII:

(Formula set out on pages following Examples) XIII but wherein T is chosen from the values defined for M, in which Rh is defined as above in part (A), by an appropriate method, as described above in part (A).

(M) For a compound of formula I in which P is a carbamoyl group of formula $CONR^2R^3$, acylation of an amine of formula $HNR^2R^3$ with a corresponding acid (or a reactive derivative thereof, including suitable esters) of formula XIV:

(Formula set out on pages following Examples) XIV but wherein T is chosen from the values defined for M. The reaction may be performed by similar procedures to those described above in part (B). For a compound of formula I in which M is a carboxy group, it is preferred to use an ester of formula XIII in which Rh is a (1-6C)alkyl group (for example, methyl) and T is a carboxy group.

(N) For a compound of formula I in which P is a IH-tetrazol-5-yl group, reacting a nitrile of formula XV:

(Formula set out on pages following Examples) XV but wherein T is chosen from the values defined for M, with an azide by similar procedures to those described above in part (E).

(O) For a compound of formula I in which P has the value $NR^4CONR^2R^3$, $OCONR^2R^3$, $NR^4COOR^5$, $NR^4COR^5$ or $OCOR^5$, acylation of a compound of formula XVI:

(Formula set out on pages following Examples) XVI but wherein T is chosen from the values defined for M and wherein QH has the value $NR^4H$ or OH, with an appropriate acylating agent, for example, an isocyanate of formula $R^2NCO$, a carbamoyl halide of formula Hal $CONR^2R^3$, a haloformate of formula Hal $COOR^5$, a mixed carbonate such as (4-nitrophenoxy)$COOR^5$, an acid halide such as Hal $COR^5$ or a mixed anhydride such as $O(COR^5)_2$.

In general, the process is performed at a temperature in the range of, for example, 0°–60° C. and conveniently in a suitable inert diluent or solvent such as dichloromethane, diethyl ether, tetrahydrofuran or dioxane. When an acid halide is used as the acylating agent, a suitable base such as triethylamine, N-methylmorpholine, piperidine or 4-(dimethylamino)pyridine is conveniently also employed.

(P) For a compound of formula I in which P has the value $S(O)_nR^5$ and n is 0, reaction of a compound of formula XVII:

(Formula set out on pages following Examples) XVII but wherein T is chosen from the values defined for M, with a mercaptan of formula $R^5SH$.

In general, the process is performed using an appropriate base, such as, for example, potassium carbonate, sodium hydroxide or sodium hydride, at a temperature in the range of, for example, 0° to 80° C., and, optionally, in a suitable inert diluent or solvent, such as, for example, acetone, tetrahydrofuran, dioxane, or N,N-dimethylformamide.

(Q) For a compound of formula I in which P has the value $S(O)_nR^5$ and n is 1 or 2, oxidation of the corresponding compound I in which n is 0 or n is 1.

In general, the process is performed at a temperature in the range of, for example, $-20°$ to 60° C. in a suitable inert diluent or solvent such as, for example, dichloromethane, tetrahydrofuran, diethyl ether or aqueous methanol, and with a suitable oxidant such as, for example, potassium peroxymonosulfate, sodium periodate or a peroxy acid such as, for example, m-chloroperbenzoic acid.

(R) For a compound of formula I wherein Ra is methyl, methylation of a corresponding compound of formula I wherein Ra is hydrogen.

In general, the process is performed using an appropriate base, such as, for example, sodium hydride, and an appropriate methylating agent, such as, for example, dimethyl sulphate or iodomethane, at a temperature in the range of, for example, 0 to 100° C., and in a suitable inert diluent or solvent, such as, for example, N,N-dimethylformamide.

It may be desired to optionally use a protecting group during all or portions of the above described processes (A)–(R); the protecting group then may be removed when the final compound is to be formed.

In general, when a compound of formula I wherein M is a carboxylic acid is required, it is preferred to carry out one of the procedures (B), (C), (D), (G), (H), (I), (J), (K), (O), (Q) and (R) mentioned above using an appropriate carboxylic ester and liberating the required acid as a final step using procedure (A) above.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures. Thus, for example, by using general procedures similar to those described in (D), (H) and (I), respectively, and by using compounds of formula VII, but wherein T is COORh, for reaction with intermediates VI, XI and XII, respectively, starting esters of formula III analogous to the compounds of formula I made by the procedures described in (D), (H) and (I) may be obtained. Similarly, by using compounds of formula VII, but wherein T is CN, for reaction with intermediates VI, XI and XII, respectively, starting nitriles of formula VIII analogous to the compounds of formula I made by the procedures described in (D), (H) and (I) may be obtained. Also, by using intermediates of respective formulae IV, V, IX, XIV, XV, XVI and XVII, but wherein T is COORh, for the general procedures described respectively in (B), (C), (G), (M), (N), (0) and (P), starting esters of formula III corresponding to the compounds of formula I made by the procedures described in (B), (C), (G), (M), (N), (0) and (P) may be obtained. Similarly, by using intermediates of the respective formulae IV, V, IX, XIII, XIV, XVI and XVII, but wherein T is CN, starting nitriles of formula VIII corresponding to the compounds of formula I made by the procedures described in (B), (C), (G), (L), (M), (0) and (P) may be obtained. Using techniques known in the art, esters of formula III wherein $>$X—Y—Z$<$ stands for $>$C=CH—N$<$ may be converted by oxidative cleavage of the unsaturated linkage into corresponding esters of formula X, but wherein T is COORh, which compounds may be further converted into intermediate esters of formula IX, but wherein T is COORh, by standard procedures known in the art. Similarly, nitriles of formula VIII wherein $>$X—Y—Z$<$ stands for $>$C=CH—N$<$ may be converted into corresponding nitriles of formula X, but wherein T is CN, and, further, into intermediates IX, but wherein T is CN. In addition, esters of formula III analogous to the compounds of formula I described in general procedures including (J), (K) and (Q) may be obtained from other esters of formula III by using similar methods to general procedures including those described in (J), (K) and (Q). Similarly nitriles of formula VIII analogous to the compounds of formula I described in general procedures including (J), (K), (L) and (Q) may be obtained from other nitriles of formula VIII by using similar methods to general procedures including those described in (J), (K), (L) and (Q).

A starting acid of formula IV, or a protected derivative thereof, may be obtained from an heterocyclic carboxylic acid of formula XVIII, or a protected derivative thereof, by using a similar procedure to (C) followed by alkylation with a compound of formula VII using a similar procedure to (D) or (I). Alternately, a similar procedure to (D) or (I) may be used first, followed by a similar procedure to (C). For a compound wherein $>$X—Y—Z$<$ stands for $>$C=N—N$<$, an acid of formula XVIII, or a protected derivative thereof, may be (i) converted to a halo acid of formula XIX, or a protected derivative thereof, (ii) substituted on nitrogen by a similar method to (C), and (iii) cross coupled with a compound of formula VII using a similar method to (H) to provide a starting acid of formula IV, or a protected derivative thereof.

A starting amide of formula V may be obtained from a compound of formula XVIII, or a protected derivative thereof, by formation of an amide by a similar method to (B) followed by alkylation with a compound of formula VII using a similar procedure to (D) or (I). Alternately, a similar procedure to (D) or (I) may be used first followe dby a similar procedure to (B). In addition, when $>$X—Y—Z$<$ is $>$N—N=C$<$, a starting amide of formula V may be obtained from an acid of formula XVIII or a protected deriative thereof, by (i) alkylation at N(1) using a similar procedure to (I); (ii) 0-benzylation at C(3)0 using a similar procedure to that described in (C) for alkylation, but using benzyl bromide in place of U.Rd as an alkylating agent: (iii) formation of an amide by a similar method to (B): and (iv) 0-debenzylation using, for example, catalytic hydrogenolysis over palladium on carbon in ethyl acetate.

A starting indole of formula VI may be obtained from 5-carboxyindole by formation of an amide by a similar method to (B) followed by alkylation of the indole by a similar method to (C).

The nitriles of formula VIII may be obtained from the corresponding compounds of formula I wherein M is carboxy by treatment with, for example, chlorosulphonyl isocyanate and N,N-dimethylformamide. Alternatively, the cyano compounds of formula VIII may be obtained by conventional dehydration of the primary amide of the corresponding carboxylic acid of formula I wherein M is carboxy.

Intermediate indazoles of formula XI may be obtained from intermediates of formula XIX by amide formation of a similar method to (B) followed by substitution at the 1-position using a similar method to (C).

Intermediate tetrahydroquinoxalines of formula XII wherein —Y—Z$<$ is —(CH$_2$)$_2$—N$<$ may be obtained from 6-carboxy-1,2,3,4-tetrahydroquinoxaline, or a protected derivative thereof, by using a similar amide formation to (B) and using a similar substitution at the 1-position to (C), in either order.

Intermediates of formulae XIII, XIV, and XV may be obtained from intermediates of formula V using similar procedures to (C); in addition, intermediates of formula XIV may be obtained from intermediates of formula XIII by a similar procedure to (A).

The intermediate alcohols and amines of formula XVI may be obtained by alkylation of the corresponding compounds of formula V with reagents of formula U.L.QH (in which QH is optionally protected) using similar procedures to those described in part (C) above.

Alternatively, the intermediate alcohols of formula XVI, but wherein Q is oxygen, may be obtained by selective reduction of the corresponding acids of formula XIV using, for example, diborane in tetrahydrofuran at ambient temperature.

The intermediates of formula XVII may be obtained from the corresponding alcohols of formula XVI, but wherein Q is oxygen, by appropriate transformations, for example, by reaction with triphenylphosphine and carbon tetrachloride or carbon tetrabromide: or by treatment with p-toluenesulphonyl chloride or methanesulphonyl chloride optionally in the presence of a suitable base, such as, for example, pyridine and in the presence of a suitable solvent or diluent such as, for example, dichloromethane.

The majority of the starting materials of formulae III, IV, V, VI, VIII, IX, X, XI, XII, XIII, XIV, XV, XVI and XVII are novel and are provided as further features of the invention based on their utility as chemical intermediates.

As stated previously, the compounds of formula I possess leukotriene antagonist properties. Thus, they antagonise the actions of one or more of the arachidonic acid metabolites known as leukotrienes, for example, $C_4$, $D_4$, and/or $E_4$, which are known to be powerful spasmogens (particularly in the lung), to increase vascular permeability and have been implicated in the pathogenesis of asthma and inflammation (see J. L. Marx, *Science*, 1982, 215, 1380-1383) as well as of endotoxic shock (see J. A. Cook, et al., *J. Pharmacol. Exp. Ther.*, 1985, 235, 470) and traumatic shock (see C. Denzlinger, et al., *Science*, 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, and psoriasis, as well as vasospastic cardiovascular disease and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I generally may be administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained by employing conventional procedures and using excipients and binders and may be administered in a variety of dosage forms. For example, the compositions may be in the form of tablets, capsules, solutions or suspensions for oral administration: in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration, the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436). Using this procedure, tracheal tissue strips are set up in groups of eight, four being used as time/vehicle (dimethyl sulfoxide) controls and four for each test compound. All of the strips are exposed to $8 \times 10^{-9}M$ leukotriene $E_4$(LTE$_4$) following the 50 minute equilibration period, and the response is recorded. This $8 \times 10^{-9}M$ concentration of LTE$_4$ is that which produces a contraction equal to about 70-80% of the maximal effect of the agonist in this tissue. The LTE$_4$ is washed out for 40-45 minutes and the procedure is repeated twice to ensure that reproducible responses are being obtained with LTE$_4$. Leukotriene $C_4$(LTC$_4$) or $D_4$(LTD$_4$), at a concentration of $8 \times 10^{-9}M$, may be substituted for LTE$_4$ in the same procedure.

Once tissue reproducibility has been established, test compounds are added to four baths following the 40-45 minute washout period. After a 10 minute incubation with test compound or vehicle, $8 \times 10^{-9}M$ LTE$_4$, LTD$_4$ or LTC$_4$ is added and the response recorded. The percentage inhibition by the test compound or the percentage change in vehicle controls is calculated, for each tissue, according to the following equation: % inhibition=100 multiplied by (mg tension increase of preceding response minus mg tension increase in presence of compound) divided by mg tension increase of preceding response. The mean percentage change for vehicle controls and test compound are calculated and evaluated for significant differences by Student's t-test for unpaired data. Tissues exposed to test compounds are retested for responsiveness to LTE$_4$, LTD$_4$ or LTC$_4$ following a 45 minute washout period. If tissue responsiveness is equal to responsiveness preceding exposure to the test compound additional studies are conducted. If responsiveness is not restored by the washing procedure, the tissues are discarded. The cyclooxygenase inhibitor, indomethancin, is present at $5 \times 10^{-6}M$ in all the determinations.

In general, the compounds of formula I tested demonstrated statistically significant activity as LTC$_4$, LTD$_4$ and/or LTE$_4$ antagonists in the above test at a concentration of about $10^{-5}M$ or much less.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}M$, again in the presence of indomethacin at $5 \times 10^{-6}M$.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before a aerosol challenge of leukotriene LTD$_4$ (starting with 3 ml of a 30 microgram/ml solution) and the effect of the test compound on the average time of leukotriene initiated change in breathing pattern (such as onset of dyspnoea) recorded and compared with that in undosed, control guineapigs. In general, compounds of formula I tested produced a significant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) all operations were carried out at room or ambient temperature, that is, t a temperature in the range of 18°-25° C.;

(ii) evaporation of solvent was carried out using a rotary evaporator under reduced pressure (600-4000 pascals; 4.5-30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. German]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnositc protons, given in parts per million (ppm) relative to tetramethylsilane (TMS) as an internal standard, determined at 80 MHz or 250 MHz using CDCl$_3$, DMSO-d$_6$ or CD$_3$OD as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used; v(volume), w(weight); mp (melting point), 1 [liter(s)], ml (milliliters), g [gram(s)], mg [milligram(s)]; and (xi) some compounds are denoted by letters, for example (A), for later reference in the Examples.

EXAMPLE 1

Methyl 4-[1-(2-carbamoylethyl)-5-(N-cyclopentrylmethylcarbamoyl)indol-3ylmethyl]-3-methoxybenzoate Silver (I) oxide (0.17 g) was added to a solution of 1-(2-carbamoylethyl)-5-(N-cyclopentylmethylcarbamoyl)indole (0.70 g) and methyl 4-bromomethyl-3methoxybenzoate (B)(0.19 g) in 1,4-dioxane (10 ml). The mixture was protected from light and stirred at 80° C. under an atmosphere of nitrogen for 12 hours. The mixture was then diluted with 1:1 v/v ethyl acetate:ether (50 ml) and filtered. The filtrate was washed sequentially with water and brine, dried (MgSO$_4$), and evaporated. The residual yellow gum was purified by flash chromatography on silica gel (500 ml), eluting with 5:95 v/v methanol:chloroform to give the title compound (0.14 g, 39%) as a white solid; mp 189°-191° C. (d); NMR (250 MHz, DMSO-d$_6$): 1.2-1.8(broad m, 8H, cyclopentyl), 2.2(sep, 1H, cyclopentylmethine), 3.2(t, 2H, CH$_2$NH), 7.2(m, 2H), 7.3(broad s, 1H, CONH$_2$), 7.5(m, 3H), 7.7(d, 1H, H$^6$-indole), 8.0(s, 1H, H$^4$-indole, 8.3 (t, 1H, NHCO).

The starting indole was prepared as follows:

(a) A solution of cyclopentylnitrile (15 g) in ether (115 ml) was added dropwise, under nitrogen, to a refluxing slurry of lithium aluminum hydride (9 g) in ether (200 ml). The mixture was treated with a saturated aqueous solution of sodium sulfate and filtered. The filtrate was dried (MgSO$_4$) and evaporated to give cyclopentylmethylamine (13 g, 84%) as a yellow liquid; IR (neat): 3300, 3340, 1600 cm$^{-1}$.

(b) A solution of cyclopentylmethylamine (2.66 g), 5-carboxyindole (4.76 g), 4-(dimethylamino)pyridine (3.60 g) and 1-(3-dimethylaminopropyl)-3-ethylcarbodiimide hydrochloride (5.67 g) in dichloromethane (60 ml) was stirred for 12 hours under an atmosphere of nitrogen. The amber solution was diluted with dichloromethane (150 ml), washed successively with 10% (w/v) aqueous sodium carbonate, 10% (v/v) hydrochloric acid, water, and brine, dried (MgSO$_4$), and evaporated. The residual amber oil was purified by flash chromatography on silica gel (700 ml), eluting with 1:3 v/v ethyl acetate:chloroform, to yield 5-(N-cyclopentylmethylcarbamoyl)indole (A) (5.17 g, 80%) as a white crystalline solid; mp 110°-112° C.; NMR (80 MHz, CDCl$_3$): 1.0-2.4(broad m, 9H, cyclopentyl), 3.4(dd, 2H, CH$_2$N), 6.2(broad, 1H, NH), 6.6(m, 1H, H$^3$-indole), 7.3(t, 1H, H$^2$-indole), 7.4(d, 1H, H$^7$-indole), 8.5(broad, 1H, CONH).

(c) A solution of 5-(N-cyclopentylmethylcarbamoyl)indole (A) (1.50 g) in N,N-dimethylformamide (DMF) (5 ml) was added to a stirred slurry of sodium hydride (0.16 g) in DMF (15 ml) maintained at 0° C. under an atmosphere of nitrogen. The mixture was warmed to room temperature for 15 minutes, treated with a solution of acrylamide (0.66 g) in DMF (5 ml), and allowed to stir for 12 hours. The mixture was poured into a cold, saturated aqueous solution of ammonium chloride to give a milky suspension which was extracted with ethyl acetate. The organic phase was washed successively with water and brine, dried (MgSO$_4$), and evaporated. The resulting clear oil was purified by flash chromatography on silica gel (700 ml), eluting with 7:93 v/v methanol:ethyl acetate, to give 1-(2-carbamoylethyl)-5-(N-cyclopentylmethylcarbamoyl)indole (0.70 g, 36%) as a gummy white foam; NMR (80 MHz, CDCl$_3$): 1.2-2.2(broad m, 9H, cyclopentyl), 2.7(t, 2H, CH$_2$CO), 3.4(dd, 2H, CH$_2$NH), 4.5(t, 2H, CH$_2$CH$_2$CO), 5.4(broad, 2H, CONH$_2$), 6.5(dd, 1H, H$^3$-indole), 7.2(d, 1H$^2$-indole), 7.3(d, 1H, H$^7$-indole), 7.6(dd, 1H, H$^6$-indole), 8.0(m, 1H, H$^4$-indole).

The starting bromoester (B) was prepared as follows:

(d) A solution of 3-methoxy-4-methylbenzoic acid (6.0 g) in methanol (120 ml) was treated with acetyl chloride (6 ml) and stirred for 36 hours. The solution was evaporated. The residue was dissolved in methanol (100 ml) and the solution evaporated. This procedure was repeated to give methyl 3-methoxy-4-methylbenzoate (6.34 g, 98%) as a colorless oil; NMR (80 MHz, CDCl$_3$): 2.2(s, 3H, CH$_3$), 3.9(2s, 6H, 2×OCH$_3$), 7.1(d, 1H), 7.5(m, 2H).

(e) A stirred solution of ester prepared according to the method described in (d) (121.2 g) in carbon tetrachloride (1.4 l) was heated under gentle reflux with a 350 watt tungsten lamp and subjected to an air purge by means of a T-tube attached to a water aspirator. A solution of bromine (107.2 g) in carbon tetrachloride (500 ml) was added dropwise over 4 hours. Evaporation of the solvent gave a light yellow solid which was triturated with 500 ml of 1:9 v/v ether:hexane. The solid was collected by filtration to give methyl 4-bromomethyl-3-methoxybenzoate (B) (111.7 g, 64%) as a pale yellow solid; mp 87°-90° C.; NMR (80 MHz, CDCl$_3$): 3.9(2s, 6H, 2×OCH$_3$), 4.5(s, 2H, BrCH$_2$), 7.4(m, 3H).

EXAMPLE 2

4[1-(2-Carbamoylethyl)-5-(N-cyclopentylmethylcarbamoyl)indol-3-ylmethyl]-3-methoxybenzoic acid A solution of methyl 4-[1-(2-carbamoylethyl)-5-(N-cyclopentylmethylcarbamoyl)indol-3-ylmethyl]-3-methoxybenzoate (0.13 g) in a combination of methanol (2 ml), tetrahydrofuran (2 ml), and water (1 ml) was treated with lithium hydroxide monohydrate (0.07 g). The mixture was stirred for 12 hours and then concentrated to remove the organic solvents. The resultant aqueous solution was acidified with 10% (v/v) hydrochloric acid. The white precipitate which formed was collected by filtration, washed with water, and dried under vacuum to give the title compound (0.10 g, 79%) as a white powder, mp 129°-131° C.

Analysis calculated for: C$_{27}$H$_{31}$N$_3$O$_5$.0.5 H$_2$O: C, 66.65; H, 6.63; N, 8.64. Found: C, 66.98; H, 6.64; N, 8.44.

EXAMPLE 3

Methyl 4-[5-(N-cyclopentylmethylcarbamoyl)-1-methyl-indol-3-ylmethyl]-3-methoxybenzoate A solution of methyl 4-[5-(N-cyclopentylmethylcarbamoyl)indol-3-ylmethyl]-3-methoxybenzoate (C) (1.52 g) in N,N-dimethylformamide (5 ml) was added to a slurry of sodium hydride (0.088 g) in N,N-dimethylformamide (3 ml) at 0° C. The mixture was stirred under a nitrogen atmosphere for 20 minutes at 0° C. and for 15 minutes at 25°0 C. The reaction was cooled to 0° C., treated with a cold solution of iodomethane (0.57 g) in N,N-dimethylformamide (2 ml), and then allowed to warm to 25°. The mixture was recooled to 0°, quenched with saturated aqueous ammonium chloride, and evaporated. The residue was dissolved in ethyl acetate, washed with water and brine, dried (MgSO$_4$), and evaporated. The amber residue was purified by flash chromatography on silica gel (500 ml), eluting with 1:9 v/v ethyl acetate:chloroform, to yield the title compound (0.86 g, 55%) as a white foam; partial NMR (80 MHz, CDCl$_3$): 3.4(dd, 2H, CH$_2$N), 3.73(s, 3H, NCH$_3$), 3.89(s, 3H, OCH$_3$), 3.92(s, 3H, OCH$_3$), 4.12(s, 2H, ArCH$_2$), 6.11(t, 1H, NH), 6.8(s, 1H, H$^2$-indole), 8.00(br s, 1H, H$^4$-indole).

The starting indole (C) was prepared according to the procedure of Example 1, starting with 5-(N-cyclopentylmethylcarbamoyl)indole (A) and methyl 4-bromomethyl-3-methoxybenzoate (B) to yield methyl 4-[5-(N-cyclopentylmethylcarbamoyl)indol-3-ylmethyl]-3-methoxybenzoate (C) (1.14 g, 33%) as a tan foam; partial NMR (80 MHz, CDCl$_3$): 3.45(dd, 2H, CH$_2$N), 3.93(s, 3H, OCH$_3$), 3.95(s, 3H, OCH$_3$), 4.17(s, 2H, ArCH$_2$), 6.17(t, 1H, NHCO), 7.01(d, 1H, H$^2$-indole), 7.16(d, 1H), 8.04(br s. 1H, H$^4$-indole), 8.45(br s, 1H, NH).

EXAMPLE 4

Methyl 4-[5-(N-cyclopentylmethylcarbamoyl)-1-[1-(N,N-dimethylcarbamoyl)ethyl]indol-3-ylmethyl]-3-methoxybenzoate Using a similar procedure to that described in Example 3, but using N,N-dimethyl-2-bromopropanamide in place of iodomethane, the title compound was obtained in 29% yield as an amber foam; partial NMR (80 MHz, CDCl$_3$): 1.62(d, 3H, CHCH$_3$), 2.78(s, 3H, NCH$_3$), 2.95(s, 3H, NCH$_3$), 3.39(dd, 2H, NCH$_2$), 3.89(s, 3H, OCH$_3$), 3.92(s, 3H, OCH$_3$), 4.11(s, 2H, ArCH$_2$) 5.29(q, 1H, CH$_3$CH), 7.01(s, 1H, H$^2$-indole).

EXAMPLE 5

Methyl 4-[5-(N-cyclopentylmethylcarbamoyl)-1-methylindazol-3-ylmethyl]-3-methoxybenzoate Methyl 4-[2-(acetyoxyimino)-2-[5-(N-cyclopentylmethylcarbamoyl)-2-methylamino)phenyl]-ethyl]-3-methoxybenzoate (63.5 mg) was placed in a 25 ml conical flask charged with a stirring bar, and the flask was maintained at 16.7 Pa by means of a vacuum pump. The flask was immersed in a preheated (200° C.) oil bath for 5 minutes, during which time the stirred solid melted and the resulting amber liquid bubbled. The cooled product was purified by flash chromatography on silica gel (300 ml), eluting with 1:3 v/v ethyl acetate:chloroform, to give the title compound (52.0 mg; 93%) as a white solid; NMR (80 MHz, CDCl$_3$): 1.2-2.0 (broad m, 9H, cyclopentyl), 3.4 (dd, 2H, CH$_2$NH), 3.9-4.0 (3s, 9H, 2×OCH$_3$, NCH$_3$) 4.4 (s, 2H, ArCh$_2$), 6.0 (broad hump, 1H, NH), 7.1-7.6 (m, 4H), 7.8 (dd, 1H, H$^6$-indole), 8.0 (broad s, 1H, H$^4$-indole).

The starting oxime-acetate was obtained as follows, starting from methyl 4-[5-(N-cyclopentylmethylcarbamoyl)-1-methylindol-3-ylmethyl]-3methoxybenzoate, itself prepared as described in Example 3:

(a) Rose Bengal (0.004 g) was added to a solution of methyl 4-[5-(N-cyclopentylmethylcarbamoyl)-1-methylindol-3-ylmethyl]-3-methoxybenzoate (0.383 g) in dry methanol (50 ml). The resulting red solution was introduced, together with a magnetic stirring bar, into a quartz photolysis apparatus fitted with a gas dispersion tube, condenser, drying tube, and a water-cooled immersion tube housing a tungsten-halogen lamp (Sylvania-GTE, type DVY, 650 watts). The stirred solution was irradiated for 1 hour while dry oxygen gas was bubbled through. Additional Rose Bengal (0.004 g) was added and the process was continued for another 50 minutes. The solution was evaporated and the vicous red residue was purified by flash chromatography on silica gel (1800 ml), eluting with 2:3 v/v chloroform:ethyl acetate, to give methyl 4-[2-[5-(N-cyclopentylmethylcarbamoyl)- 2-(formyl) (methyl)aminophenyl]-2-oxoethyl]-3-methoxybenzoate (0.156 g, 43%) as a viscous orange oil; NMR (250 MHz, CDCl$_3$): 1.2-1.8[8H, (CH$_2$)$_4$], 2.1 (m, 1H, CHCH$_2$N), 3.25 (s, 2.1 H, NCH$_3$, isomer A), 3.35 (s, 0.9H, NCH$_3$, isomer B), 3.42 (dd, 2H, CH$_2$NH), 3.81 (s, 2.1H, OCH$_3$, isomer A), 3.88 (s, 0.9H, OCH$_3$, isomer B), 3.91(s, 3H, CO$_2$CH$_3$), 4.14 (s, 1.4H, ArCH$_2$CO, isomer A), 4.30 (s, 0.6H, ArCH$_2$CO, isomer B), 6.2 (broad t, 1H, NH), 7.2-8.3 (7H).

(b) A solution of methyl 4-[2-[5-(N-cyclopentylmethylcarbamoyl)-2-(formyl) (methyl)aminophenyl]-2-oxoethyl]-3-methoxybenzoate (0.142 g) and hydroxylamine hydrochloride (0.13 g) in freshly distilled, dry pyridine (10 ml) was heated and stirred under reflux for 12 hours under an atmosphere of nitrogen. The cooled solution was filtered, and the filtrate was concentrated. The resulting amber oil was dissolved in ethyl acetate, and this solution was washed with water, dried (MgSO$_4$), and evaporated. The residue was purified by flash chromatography on silica gel (1200 ml), eluting with 2:3 v/v ethyl acetate: chloroform, to give methyl 4-[2-[5-(N-cyclopentylmethylcarbamoyl)-2-methylaminophenyl]-2-(hydroxyimino)-ethyl]-3-methoxybenzoate (0.88 g; 65%) as a pink solid; NMR (250 MHz, CDCl$_3$): 1.2–1.8[8H, (CH$_2$)$_4$], 2.0 (m, 1H, CHCH$_2$N), 2.9 (d, 3H, NCH$_3$), 3.3 (dd, 2H, CH$_2$N), 3.9 (s, 3H, OCH$_3$), 4.0 (s, 3H, OCH$_3$), 4.3 (s, 2H, ArCH$_2$), 5.8 (broad t, 1H, NHCO), 8.6 (d, 1H), 7.1 (d, 1H), 7.5–7.8 (4H), 8.0 (broad q, 1H, CH$_3$NH).

(c) A solution of methyl 4-[2-[5-(N-cyclopentylmethylcarbamoyl)-2-methylaminophenyl]-2-(hydroxyimino)ethyl]-3-methoxybenzoate (79.9 mg), 4-(dimethylamino)pyridine (22 mg), and acetic anhydride (0.17 ml) in dischloromethane (11 ml) was stirred under a nitrogen atmosphere for 15 hours. The solution was diluted with dischloromethane, washed with 5% w/v sodium hydrogen sulfate, water, and brine, then dried (MgSO$_4$), and evaporated to give methyl 4-[2-(acetoxyimino)-2-[5-(N-cyclopentylmethylcarbamoyl)-2-methylaminophenyl]ethyl]-3-methoxybenzoate (74.1 mg, 85%) as a pink solid; NMR (80 MHz, CDCl$_3$): 1.2–1.8 [8H, (CH$_2$)$_4$], 2.1 (s, 3H, CH$_3$CO), 3.0 (d, 3H, NCH$_3$), 3.3. (dd, 2H, CH$_2$NH), 3.9 (2s, 6H 2×OCH$_3$), 4.3(s, 2H, ArCH$_2$), 5.8 (broad, 1H, NHCO), 6.7(d, 1H), 7.0 (d, 1H), 7.4–7.6 (m, 3H), 7.8 (d, 1H), 8.5 (broad, 1H, CH$_3$NH).

EXAMPLE 6

4-[5-(N-Cyclopentylmethylcarbamoyl)-1-methylindol-3-ylmethyl]-3-methoxybenzoic acid Using a similar procedure to that described in Example 2, except starting from the ester described in Example 3 and washing the alkaline solution with ethyl acetate before acidification, the title compound was obtained in 89% yield as an ivory solid; mp 237°–239° C.

Analysis calculated for: C$_{25}$H$_{28}$N$_2$O$_4$.0.3 C$_4$H$_8$O$_2$: C, 70.41; H, 6.86; N, 6.27. Found: C, 70.08; H, 6.82; N, 6.55.

EXAMPLE 7

4-[5-(N-Cyclopentrylmethylcarbamoyl)-1-[1-(N,N-dimethylcarbamoyl)ethyl]indol-3-ylmethyl]-3-methoxybenzoic acid Using a similar procedure to that described in Example 2, except starting from the ester described in Example 4, the title compound was obtained in 59% yield as an ivory solid; mp 146°–147° C.

Analysis calculated for: C$_{29}$H$_{35}$N$_3$O$_5$. 0.5 H$_2$O: C, 67.68; H, 7.05; N, 8.16. Found: C, 67.67; H, 6.89; N, 7.92.

EXAMPLE 8

4-[5-(N-Cyclopentylmethylcarbamoyl)-1-methylindazol-3-ylmethyl]-3-methoxybenzoic acid Using a similar procedure to that described in Example 2, except starting from the ester described in Example 5, the title compound was obtained in 90% yield as a white solid; mp 240°–242° C. (d).

Analysis calculated for:
C$_{24}$H$_{27}$N$_3$O$_4$.0.2 H$_2$O: C, 67.81; H, 6.50; N, 9.88. Found: C, 67.61; H, 6.45; N, 9.73.

EXAMPLE 9

N-[4-[1-(2-Carbamoylethyl)-5-(N-cyclopentylmethyl carbamoyl)indol-3-ylmethyl]-3-methoxybenzoyl]-2-methylbenzenesulphonamide A solution of 4-[1-(2-carbamoylethyl)-5-(N-cyclopentylmethylcarbamoyl)indol-3-ylmethyl]-3-methoxybenzoic acid (77 mg), 4-(dimethylamino)pyridine (20 mg), 1-(3-dimethylaminopropyl)-3-ethylcarbodiimide hydrochloride (37 mg), and ortho-toluenesulphonamide (28 mg) in dichloromethane (2.0 ml) was stirred under a nitrogen atmosphere for 48 hours. The mixture was diluted with dichloromethane; washed with 10% v/v hydrochloric acid, water, and brine; and evaporated. The resulting white solid was crystallized from ethyl acetate/hexane to give the title compound (37 mg; 37%) as a white solid; mp 140°–145° C. (d).

Analysis calculated for: C$_{34}$H$_{38}$N$_4$O$_6$S.1.0 H$_2$O: C, 62.94; H, 6.21; N, 8.64. Found: C, 63,10; H, 6.14; N, 8.24.

EXAMPLE 10

N-[4-[5-(N-Cyclopentylmethylcarbamoyl)-1-methylindol-3-ylmethyl]-3-methoxybenzoyl-2-methylbenzenesulphonamide Using a similar procedure to that described in Example 9, except starting from the acid described in Example 6, the title compound was obtained as an ivory powder (51%); mp 152°–154° C.

Analysis calculated for: C$_{32}$H$_{35}$N$_3$O$_5$S.O.7 H$_2$O: C, 65.55; H, 6.26; N, 7.17. Found: C, 65.36; H, 6.19, N, 7.53.

EXAMPLE 11

N-[4-[5-(N-Cyclopentrylmethylcarbamoyl)-1-[1-(N,N-dimethylcarbamoyl)ethyl]indol-3-ylmethyl]-3-methoxy benzoyl]-2-methylbenzenesulphonamide Using a similar procedure to that described in Example 9, except starting from the acid described in Example 7, the title compound was obtained as an ivory powder (68%); mp 144°–145° C.

Analysis calculated for: C$_{36}$H$_{42}$N$_4$O$_6$S.1.2 H$_2$O: C, 63,54; H, 6.20; N, 8.16. Found: C, 63.31; H, 6.20; N, 8.16.

EXAMPLE 12

Methyl 4-[1-methyl-5-[N-(3-methylbutyl)carbamoyl]indol-3-ylmethyl]-3-methoxybenzoate Using a similar procedure to that described in Example 3, but starting from methyl 4-[5-[N-(3-methylbutyl)-carbamoyl]indol-3-ylmethyl]-3-methoxybenzoate (E), the title compound was obtained in 29% yield as a white solid; partial NMR (80 MHz, CDCl$_3$): 0.95[d, 6H, CH(CH$_3$)$_2$], 3.47(q, 2H, NCH$_2$), 3.73(s, 3H, NCH$_3$), 3.88(s, 3H, OCH$_3$), 3.92(s, 3H, OCH$_3$), 4.12(s, 2H, ArCH$_2$), 6.01(br t, 1H, NH), 6.79(s, 1H, H$^2$-indol).

The starting indole (E) was prepared as follows:
a) Using a similar procedure to that described in Example 1, part b, but using with 3-methylbutylamine in place of cyclopentylmethylamine, there was obtained 5-[N-(3-methylbutyl)carbamoyl]-indole (F) in 72% yield as a white oslid; partial NMR (80 MHz, CDCl$_3$):

0.96[d, 6H, CH(CH$_3$)$_2$], 3.50(q, 2H, NCH$_2$), 6.09(br t, 1H, CONH), 6.60(br s, 1H, H$^3$-indole), 7.37(d, 1H, H$^6$-indole), 8.06(s, 1H, H$^4$-indole), 8.54(br s, 1H, NH).

b) Silver(I) oxide (4.92 g) was added to a solution of indole (F) (2.05 g) in toluene (15 ml). The mixture was protected from light, stirred, and heated to reflux under an atmosphere of nitrogen for 24 hours. A soution of methyl 4-bromomethyl-3-methoxybenzoate (B) (2.31 g) in toluene (5 ml) was added, and stirring was continued at 95° C. for 4 hours. The mixture was then diluted with ethyl acetate and filtered. The filtrate was evaporated to give an amber gum which was purified by flash chromatography on silica gel (862 ml), eluting with 1:99 v/v methanol:chloroform to give (E) (0.47 g, 13%) as a white foam; partial NMR (80 MHz, CDCl$_3$): 0.92[d, 6H, CH(CH$_3$)$_2$], 3.40(q, 2H, NCH$_2$), 3.87(s, 3H, OCH$_3$), 4.09(s, 2H, ArCH$_2$), 6.18(br t, 1H, CONH), 7.98(br s, 1H, H$^4$-indole), 8.84(br s, 1H, NH).

EXAMPLE 13

4-[1-Methyl-5-[N-(3-methylbutyl)carbamoyl]indol-3-ylmethyl]-3-methoxybenzoic acid Using a similar procedure to that described in Example 2, except starting from the ester described in Example 12, the title compound was obtained in 67% yield as a white solid; mp 190°-191° C.

Analysis calculated for: C$_{24}$H$_{28}$N$_2$O$_4$: C, 70.57; H, 6.91; N, 6.86. Found: C, 70.63; H, 6.96; N, 6.70.

EXAMPLE 14

Methyl 4-[5-[N-(cyclopentylmethyl)-N-methylcarbamoyl]-1-methylindol-3-ylmethyl]-3-methoxybenzoate Silver(I) oxide (0.30 g) was added to a solution of 5-[N-(cyclopentylmethyl)-N-methylcarbamoyl]-1-methylindole (G) (0.35 g) in dioxane (2 ml). The mixture was protected from light, stirred, and heated to reflux under an atmosphere of nitrogen for 2 hours. A solution of methyl 4-bromomethyl-3-methoxybenzoate (B) (0.33 g) in dioxane (1 ml) was added and the mixture was heated to reflux for an additional 18 hours. The mixture was then diluted with ethyl acetate and filtered. The filtrate was evaporated to give an amber gum which was purified by flash chromatography on silica gel (223 ml), eluting with chloroform to give the title compound (75.2 mg, 13%) as a white foam; partial nmr (80 MHz, CDCl$_3$): 3.01(s, 3H, CONCH$_3$), 3.51(br d, 2H, NCH$_2$), 3.74(s, 3H, NCH$_3$), 3.89(s, 3H, OCH$_3$), 3.92(s, 3H, OCH$_3$), 4.10(s, 2H, ArCH$_2$), 6.81(s, 1H, H$^2$-indole).

Starting indole (G) was prepared as follows:

A solution of 5-[N-(cyclopentylmethyl)carbamoyl]indole (A) (0.76 g) in N,N-dimethylformamide (6 ml) was added to a slurry of sodium hydride (0.18 g) in N,N-dimethylformamide (6 ml) at 0°. The mixture was stirred under a nitrogen atmosphere for 5 minutes at 0° C. and 60 minutes at 25° C. The reaction was recooled to 0° C., treated with a solution of dimethyl sulphate (0.88 g) in N,N-dimethylformamide (5 ml), and then stirred at 80° C. for 18 hours. The mixture was quenched with saturated aqueous ammonium chloride, and extracted with ethyl acetate. The organic phase was washed with water and brine, dried (MgSO$_4$), and evaporated. The resulting amber oil was purified by flash chromatography on silica gel (144 ml), eluting with 1:9 v/v ethyl acetate:chloroform, to give (G) (0.35 g, 39%) as an amber oil; partial NMR (80 MHz, CDCl$_3$): 3.04(s, 3H, CONCH$_3$), 3.42(br d, 2H, NCH$_2$), 3.78(s, 3H, NCH$_3$), 6.49(d, 1H, H$^3$-indole), 7.06(d, 1H, H$^2$-indole), 7.26(m, 2H, Ar), 7.66(s, 1H, H$^4$-indole).

EXAMPLE 15

4[5-N-Cyclopentylmethyl-N-methylcarbamoyl]-1-methyl indol-3-ylmethyl]-3-methoxybenzoic acid Using a similar procedure to that described in Example 2, except starting from the ester described in Example 14, the title compound was obtained in 45% yield as an ivory solid; mp 112–11420 C.

Analysis calculated for C$_{26}$H$_{30}$N$_2$O$_4$.3 H$_2$O: C, 70.98; H, 7.01; N, 6.37. Found: C, 70.77; H, 6.89; N, 6.22.

EXAMPLE 16

The following illustrates representative pharmaceutical dosages forms which may be used for the therapeutic or prophylactic administration of an acidic compound of formula I (that is, M is an acidic group as defined hereinbefore) or of a pharmaceutically acceptable salt thereof (hereinafter referred to as 'Compound X'):

| (i) | Tablet 1 | mg/tablet |
|---|---|---|
| | 'Compound X' | 100 |
| | Lactose | 182.75 |
| | Croscarmellose Sodium | 12.0 |
| | Starch | 2.25 |
| | Magnesium stearate | 3.0 |
| (ii) | Tablet 2 | mg/tablet |
| | 'Compound X' | 20 |
| | Microcrystalline cellulose | 420 |
| | Polyvinylpyrrolidone | 14.0 |
| | Starch | 43.0 |
| | Magnesium stearate | 3.0 |
| (iii) | Capsule | mg/capsule |
| | 'Compound X' | 10 |
| | Lactose | 488.5 |
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1M Sodium hydroxide solution | 15.0% w/v |
| | Water for injection . . . to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 3.5% w/v |
| | Water for injection . . . to 100% | |
| (vi) | Aerosol | mg/ml |
| | 'Compound X' | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well known pharmaceutical techniques to accommodate differing amounts and types of active ingredient 'Compound X'. The aerosol (vi) may be used in conjunction with a standard, metered dose aerosol dispenser.

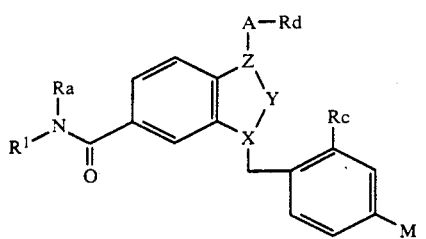 I
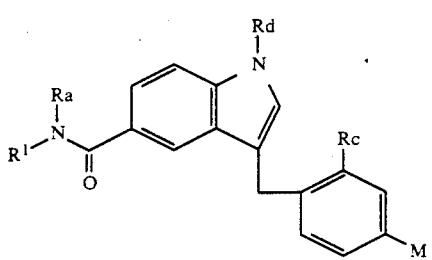 Ia
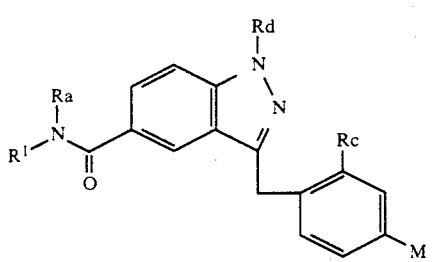 Ib
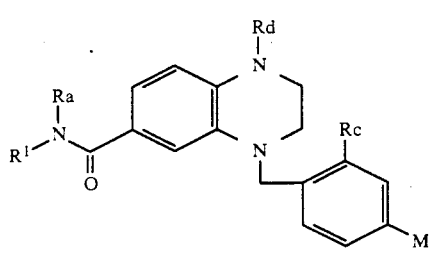 Ic
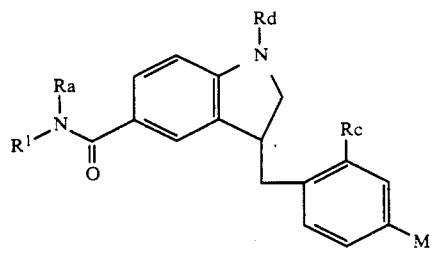 Id
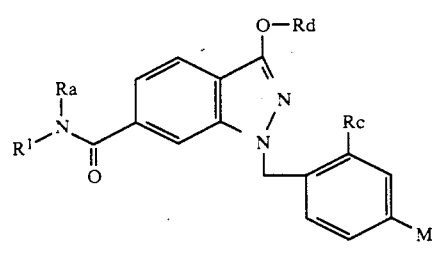 Ie
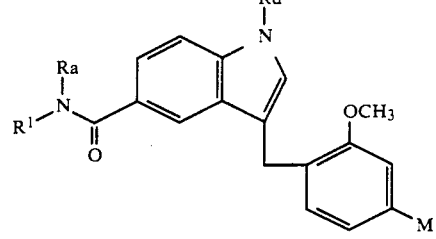 IIa
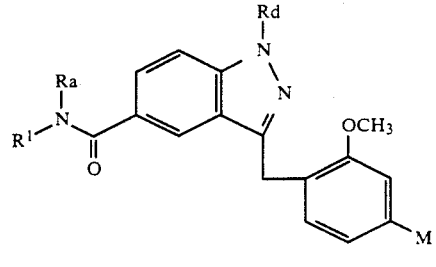 IIb
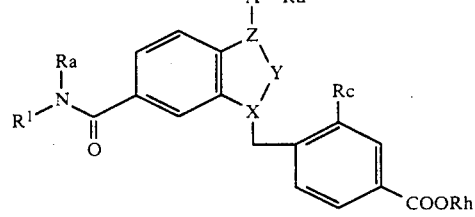 III
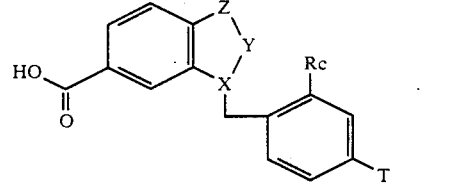 IV
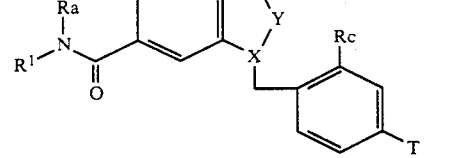 V
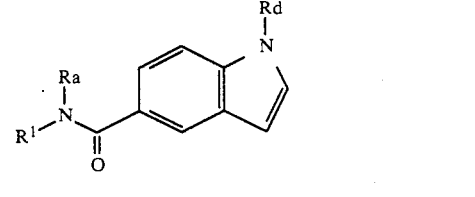 VI
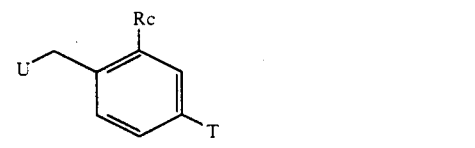 VII

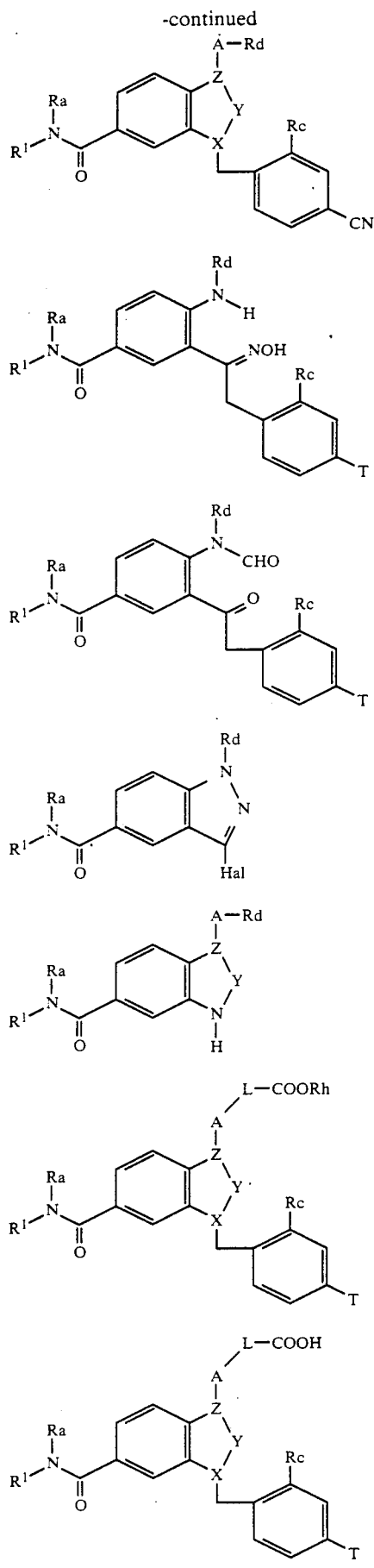
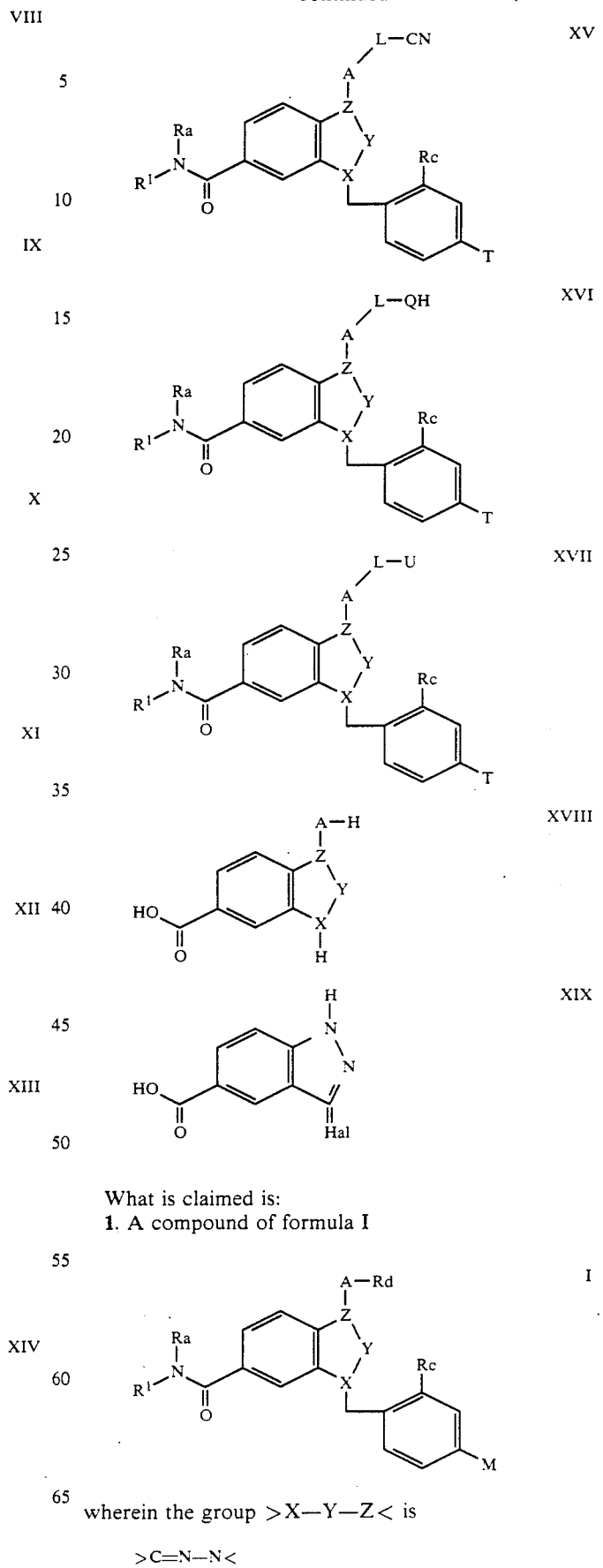
What is claimed is:
1. A compound of formula I
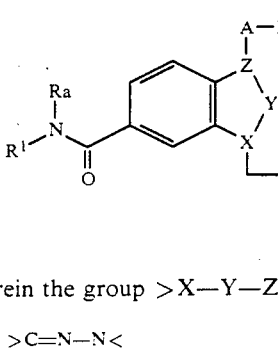
wherein the group >X—Y—Z< is
>C=N—N< wherein:

A is a direct link;

R¹ is selected of from a group consisting of (2-10C)alkyl optionally containing 1 or more fluorine substituents; phenyl-(1-6C)alkyl in which the (1-6C)alkyl moiety may optionally bear a fluoro or (1-4C)alkoxy substituent and in which the phenyl moiety may optionally bear a substituent selected from a group consisting of halogeno, (1-4C)alkyl, (1-4C)alkoxy and trifluoromethyl; (3-8C)cycloalkyl and (3-8C)cycloalkyl-(1-6C)alkyl, the cyclic moiety of any of which optionally may contain one unsaturated linkage and may optionally bear 1 or 2 (1-4C)alkyl substituents;

Ra is hydrogen or methyl;

Rc is selected from a group consisting of hydrogen and (1-4C)alkoxy;

Rd is hydrogen, (3-8C)cycloalkyl, (3-8C)cycloalkyl-(1-4C)alkyl or (1-10C)alkyl optionally containing one or two double or triple bonds, said (1-10C)alkyl additionally optionally bearing a substituent P selected from a group consisting of cyano, carboxy, (1-4C)alkoxycarbonyl, carbamoyl of formula CONR²R³, ureido of formula NR⁴CONR²R³, carbamoyloxy of formula OCONR²R³, a carbamate of formula NR⁴COOR⁵, acylamino of formula NR⁴COR⁵, acyloxy of formula OCOR⁵, and an (optionally oxidized) thio group of formula $(S(O)_nR^5$ in which R² is selected from a group consisting of hydrogen, (1-6C)alkyl, and phenyl, the phenyl, the phenyl moiety of which may optionally bear 1 or 2 substituents selected from a group consisting of halogeno, (1-4C)alkyl, (1-4C)alkoxy and trifluoromethyl; R³ and R⁴ are independently chosen from a group consisting of hydrogen and (1-6C)alkyl; R⁵ is selected from a group consisting of (1-4C)alkyl and phenyl wherein the phenyl moiety may optionally bear 1 or 2 substituents selected from a group consisting of halogen, (1-4C)alkyl, (1-4C)alkoxy and trifluoromethyl; and n is the integer 0, 1 or 2; and M is an acidic group selected from a group consisting of carboxy and an acylsulphonamide residue of formula —CO NH SO₂R⁶ in which R⁶ is selected from a group consisting of (1-6C)alkyl, (3-8C)cycloalkyl, (6-12C)aryl, and (6-12C)aryl-(1-4C)alkyl, in which any of the aromatic moieties may bear 1 or 2 substituents selected from a group consisting of halogeno, amino, (1-4C)alkyl, (1-4C)alkoxy, and trifluoromethyl;

or a pharmaceutically acceptable salt thereof.

2. A compound as claimed in claim 1 wherein:

R¹ is selected form a group consisting of (3-7C) alkyl optionally containing 1 or more fluorine substituents; phenyl-(1-4C)alkyl in which the (1-4C)alkyl moiety may optionally bear a fluoro or (1-4C)alkoxy substituent and in which the phenyl moiety may optionally bear a substituent selected from a group consisting of halogeno, (1-4C)alkyl, (1-4C)alkoxy and trifluoromethyl; (3-6C)cycloalkyl and (3-6C)cycloalkyl-(1-4C)alkyl, the cyclic moiety of any of which optionally may contain one unsaturated linkage and may optionally bear 1 or 2 (1-4C)alkyl substituents;

Ra is hydrogen;

Rd is hydrogen, (3-6C)cycloalkyl, (3-6C)cycloalkyl-(1-2C)alkyl or (1-5C)alkyl optionally containing one double or triple bond, said (1-5C)alkyl additionally optionally bearing a substitutent P selected from a group consisting of cyano, carboxy, (1-2C)alkoxycarbonyl, carbamoyl of formula CONR²R³, and an oxidized thio group of formula $S(O)_nR^5$ in which R² is selected from a group consisting of hydrogen, (1-4C)alkyl, and phenyl, the phenyl moiety of which may optionally bear 1 or 2 substituents selected from a group consisting of halogeno, (1-4C)alkyl, (1-4C)alkoxy and trifluoromethyl, and R³ is chosen from a group consisting of hydrogen and (1-4C)alkyl; R⁵ is selected from a group consisting of (1-4C)alkyl and phenyl wherein the phenyl moiety may optionally bear 1 or 2 substituents selected from a group consisting of halogen, (1-4C)alkyl, (1-4C)alkoxy and trifluoromethyl; and n is the integer 1 or 2; and M is an acidic group selected from a group consisting of carboxy, and an acylsulphonamide residue of formula —CO NH SO₂R⁶ in which R⁶ is selected from a group consisting of (1-4C)alkyl, (3-6C) cycloalkyl, and phenyl, in which the phenyl may bear 1 or 2 substituents selected from a group consisting of halogeno, amino, (1-4C)alkyl, (1-4C)alkoxy, and trifluoromethyl.

3. A compound as claimed in claim 2 wherein:

R² and R³ are independently selected from a group consisting of hydrogen and (1-4C)alkyl;

R⁵ is (1-4C)alkyl;

n is the integer 1 or 2; and

R⁶ is selected from a group consisting of (1-4C)alkyl, and phenyl, in which the phenyl may bear 1 or 2 substituents selected form a group consisting of halogeno, amino, (1-4C)alkyl, (1-4C)alkoxy, and trifluoromethyl.

4. A compound as claimed in claim 1 wherein M is carboxy[, 1H-tetrazol-5-yl] or a radical of formula —CO NH SO₂R⁶ wherein R⁶ is phenyl, optionally substituted as defined in claim 1.

5. A compound as claimed in claim 1 which is an indazole of formula IIb:

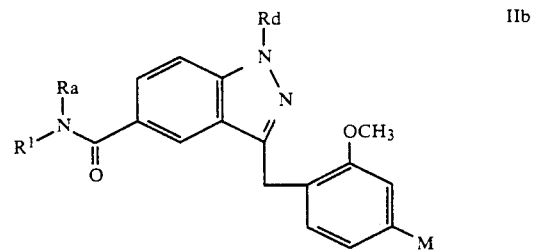

wherein R¹, Ra, Rd and M have any of the meanings defined in claim 1.

6. A compound as claimed in claim 1 wherein R¹ is selected from a group consisting of (a) ethyl, propyl, isopropyl, butyl, isobutyl, sec-butyl, t-butyl, pentyl, 3-methylbutyl, 1-ethylpropyl, hexyl, heptyl, 1-ethylpentyl, and nonyl, each of which may optionally be substituted by 1 or more fluorine substituents;

(b) benzyl, 1-phenylethyl, 2-phenylethyl, 1-phenylpropyl, 2-phenylpropyl, 3-phenylpropyl, 1-methyl-1-phenylethyl, 1-phenylpropyl, 1-phenylbutyl, and 1-phenylpentyl, each of which optionally may be substituted on the alkyl portion by methoxy or ethoxy and each of which may optionally be substituted on the phenyl moiety by a member selected from a group consisting of fluoro, chloro, bromo, methyl, ethyl, methoxy and ethoxy;

(c) cyclopropyl, cyclobutyl, cyclopentyl, cyclohexyl, cycloheptyl, cyclobutylmethyl, cyclopentylmethyl, cyclohexlmethyl, 1-cyclopentylethyl, 2-cyclopentyl-ethyl, 1-cyclopentylpropyl, 1-cyclopentylbutyl, and 1-cyclohexylbutyl wherein each of the cyclic may optionally be substituted by methyl, ethyl or isopropyl; and (d) cyclopentenyl, cyclohexenyl, cyclopentenyl-(1-6C)-alkyl, and cyclohexenyl-(1-6C)alkyl wherein each of the cyclic moieties may optionally be substituted by methyl, ethyl or isopropyl;

Rc is methoxy or ethoxy;

Rd is selected from a group consisting of cyclopropyl, cyclopentyl, cyclohexyl, cyclopropylmethyl, cyclopentylmethyl, cyclohexylmethyl, methyl, ethyl, propyl, isopropyl, butyl, isobutyl, sec-butyl, 3-methylbutyl, pentyl, hexyl, vinyl, allyl, 1-propenyl, 2-methylallyl, 3-methylbut-2-enyl, 1,3-butadienyl, 1,3-pentadienyl, 2-propynyl, and 3-butynyl, each of said alkyl groups additionally optionally bearing the substituent P;

$R^2$, $R^3$, and $R^4$, when the particular group is (1-6C)alkyl are independently selected from a group consisting of methyl, ethyl propyl, isopropyl, butyl, t-butyl and pentyl;

$R^5$ is methyl, ethyl, propyl or isopropyl;

$R^6$ is methyl, ethyl, propyl, isopropyl, butyl, cyclopentyl, cyclohexyl, phenyl, 1-naphthyl, 2-naphthyl, benzyl, 1-naphthylmethyl or 2-naphthylmethyl wherein each aromatic moiety may be optionally substituted as defined in $R^1$ for a phenyl moiety.

7. A compound as claimed in claim 1 wherein:

$R^1$ is ethyl, propyl, isopropyl, butyl, isobutyl, sec-butyl, t-butyl, pentyl, 3-methylbutyl, 1-ethylpropyl, hexyl, heptyl, 1-ethylpentyl, nonyl, benzyl, 4-chlorobenzyl, 4-trifluoromethylbenzyl, 4-methylbenzyl, 1-phenylethyl, 2-phenylethyl, 1-methyl-1-phenylethyl, 1-phenylpropyl, 1-phenylpentyl, cyclopentyl, cyclohexyl, cyclobutylmethyl, cyclopentylmethyl, cyclohexylmethyl, 2-cyclopentylethyl, 1-cyclopentylbutyl, 1-cyclohexylpropyl, 1-cyclohexylbutyl, cyclopentenylmethyl, or 1-cyclohexen-4-ylmethyl;

Rc is hydrogen or methoxy;

Rd is methyl, ethyl, propyl, butyl, vinyl, allyl, 1-propenyl, 1,3-butadienyl or 2-propynyl, said group additionally optionally bearing the substituent P;

$R^2$ is hydrogen, methyl, ethyl, propyl, isopropyl, t-butyl, phenyl, 2-methylphenyl or 4-chlorophenyl and $R^3$ and $R^4$ are each independently selected to be hydrogen, methyl or ethyl;

$R^5$ is methyl, ethyl, propyl, isopropyl, phenyl, 2-methylphenyl or 4-chlorophenyl; and $R^6$ is methyl, isopropyl, butyl, cyclopentyl, phenyl, 4-chlorophenyl, 4-methylphenyl, 2-chlorophenyl, 2-aminophenyl, 2-methylphenyl, 2-methoxypehnyl, or 2-naphthyl.

8. A compound of formula III:

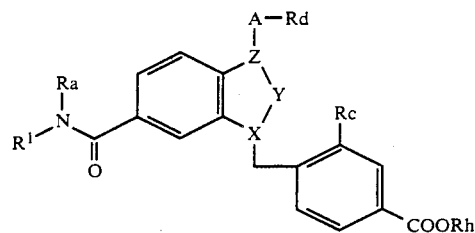

wherein Rh is benzyl, phenyl or (1-6C)alkyl optionally bearing an acetoxy, (1-4C)alkoxy or (1-4C)alkylthio substituent; and wherein the group >X—Y—Z< is >C=N—N< wherein:

A is a direct link;

$R^1$ is selected from a group consisting of (2-10C)alkyl optionally containing 1or more fluorine substituents; phenyl-(1-6C)alkyl in which the (1-6C)alkyl moiety may optionally bear a fluoro or (1-4C)alkoxy substituent and in which the phenyl moiety may optionally bear a substituent selected from a group consisting of halogeno, (1-4C)alkyl, (1-4C)alkoxy and trifluoromethyl; (3-8C) cycloalkyl and (3-8C)cycloalkyl-(1-6C)alkyl, the cyclic moiety of any of which optionally may contain one unsaturated linkage and may optionally bear 1 or 2 (1-4C)alkyl substituents;

Ra is hydrogen or methyl;

Rc is selected from a group consisting of hydrogen and (1-4C)alkoxy;

Rd is hydrogen, (3-8C)cycloalkyl, (3-8C)cycloalkyl-(1-4C)alkyl or (1-10C)alkyl optionally containing one or two double or triple bonds, said (1-10C)alkyl additionally optionally bearing a substitutent P selected from a group consisting of cyano, carboxy, (1-4C)alkoxycarbonyl, carbamoyl of formula $CONR^2R^3$, ureido of formula $NR^4CONR^2R^3$, carbamoyloxy of formula $OCONR^2R^3$, a carbamate of formula $NR^4COOR^5$, acylamino of formula $NR^4COR^5$, acyloxy of formula $OCOR^5$, and an (optionally oxidized) thio group of formula $S(O)_nR^5$ in which $R^2$ is selected from a group consisting of hydrogen, (1-6C)alkyl, and phenyl, the phenyl moiety of which may optionally bear 1 or 2 substituent selected from a group consisting of halogene, (1-4C)alkyl, (1-4)alkoxy and trifluoromethyl; $R^3$ and $R^4$ are independently chosen from a group consisting of hydrogen and (1-6C)alkyl; $R^5$ is selected from a group consisting of (1-4C)alkyl and phenyl wherein the phenyl wherein the phenyl moiety may optionally bear 1 or 2 substituents selected from a group consisting of halogen, (1-4C)alkyl (1-4C)alkoxy and trifluoromethyl; and n is the integer 0, 1 or 2.

9. A pharmaceutical composition comprising a leukotriene antagonizing amount of a compound of claim 1 or a pharmaceutically acceptable salt thereof and a nontoxic pharmaceutically acceptable diluent or carrier.

10. A method of antagonizing the action of at least one type of leukotriene in a mammal comprising administering to the mammal a pharmaceutically effective amount of a compound of claim 1.

11. A method for the treatment of a selected allergic or inflammatory disorder in a mammal comprising administering a pharmaceutically effective amount of a compound of claim 1 to a mammal in need of such treatment.

12. A composition as claimed in claim 9 wherein said composition is in the form of a liquid or powdered aerosol.

* * * * *